(12) United States Patent
Roeske et al.

(10) Patent No.: US 10,856,835 B2
(45) Date of Patent: Dec. 8, 2020

(54) PHANTOMS AND METHODS OF CALIBRATING DUAL ENERGY IMAGING SYSTEMS THEREWITH

(71) Applicant: Loyola University Chicago, Maywood, IL (US)

(72) Inventors: John C. Roeske, Naperville, IL (US); Rakesh Patel, Chicago, IL (US); Maksat Haytmyradov, Oak Park, IL (US)

(73) Assignee: Loyola University Chicago, Maywood, IL (US)

( * ) Notice: Subject to any disclaimer, the term of this patent is extended or adjusted under 35 U.S.C. 154(b) by 0 days.

(21) Appl. No.: 16/511,182

(22) Filed: Jul. 15, 2019

(65) Prior Publication Data
US 2020/0015772 A1 Jan. 16, 2020

Related U.S. Application Data

(60) Provisional application No. 62/697,482, filed on Jul. 13, 2018.

(51) Int. Cl.
*G01D 18/00* (2006.01)
*A61B 6/00* (2006.01)

(52) U.S. Cl.
CPC ............ *A61B 6/583* (2013.01); *A61B 6/482* (2013.01); *A61B 6/505* (2013.01)

(58) Field of Classification Search
CPC ......... A61B 6/583; A61B 6/482; A61B 6/505; A61N 5/2075; A61N 2005/1076
See application file for complete search history.

(56) References Cited

U.S. PATENT DOCUMENTS

| 5,335,260 A | 8/1994 | Arnold |
| 5,481,587 A | 1/1996 | Mazess |
| 6,302,582 B1 | 10/2001 | Nord et al. |
| 6,315,447 B1 | 11/2001 | Nord et al. |

(Continued)

FOREIGN PATENT DOCUMENTS

| JP | 2013176694 | 9/2013 |
| KR | 101698033 | 1/2017 |
| KR | 20180060879 | 6/2018 |

OTHER PUBLICATIONS

International Search Report for International Application No. PCT/US2019/041814, dated Oct. 31, 2019, 3 pages.

*Primary Examiner* — Kiho Kim
(74) *Attorney, Agent, or Firm* — Hartman Global IP Law; Gary M. Hartman; Domenica N. S. Hartman

(57) ABSTRACT

Phantoms for use in calibrating a dual energy imaging system and methods for their use. The phantoms include a body having at least first and second portions arranged in a through-thickness direction of the body. The first portion defines an anterior surface of the body and contains a first material simulating soft tissue and a second material simulating bone. The second portion contains a third material simulating lung tissue and at least a first object embedded in the third material and formed of a fourth material simulating tumor tissue. The first and second portions of the body are configured such that the second material in the first portion superimposes the first object in the second portion in the through-thickness direction of the body relative to the anterior surface thereof.

19 Claims, 3 Drawing Sheets

(56) References Cited

U.S. PATENT DOCUMENTS

| | | | |
|---|---|---|---|
| 2003/0072417 A1* | 4/2003 | Kaufhold | A61B 6/583 378/207 |
| 2012/0014584 A1 | 1/2012 | Han et al. | |
| 2014/0243579 A1 | 8/2014 | Roeske et al. | |
| 2017/0186195 A1* | 6/2017 | Lin | A61B 6/5282 |

* cited by examiner

PHANTOMS AND METHODS OF CALIBRATING DUAL ENERGY IMAGING SYSTEMS THEREWITH

CROSS-REFERENCE TO RELATED APPLICATIONS

This application claims the benefit of U.S. Provisional Application No. 62/697,482, filed Jul. 13, 2018, the contents of which are incorporated herein by reference.

BACKGROUND OF THE INVENTION

The present invention generally relates to calibration of medical imaging equipment. The invention particularly relates to methods and phantoms for calibration and quality assurance of dual energy subtraction equipment used for radiation therapy.

Recently, there has been interest in real-time lung tumor tracking during radiation treatment delivery. The goal is to modify the treatment (e.g., multi-leaf collimators, treatment table position, etc.), based on the position of the tumor during respiration, to minimize the volume of normal tissue irradiated. One approach involves the use of dual energy (DE) imaging to increase the likelihood of successful and accurate markerless tumor tracking. Briefly, DE imaging involves obtaining x-ray images at both high (e.g., 120 kVp) and low (e.g., 60 kVp) energies. By performing weighted logarithmic subtraction (WLS), a third image is created that suppresses bone and enhances soft tissue/tumor. The purpose of this subtraction is to remove bone that may obscure visualization of tumors (typically of the lung) on planar radiographs.

To implement dual energy subtraction imaging efficiently, imaging parameters (e.g., kVp, mA) are preferably optimized, that is, the equipment is calibrated to promote clear imaging. It would be desirable if a standardized methodology of calibration were available that could be routinely performed and verified for quality assurance purposes.

BRIEF DESCRIPTION OF THE INVENTION

The present invention provides phantoms and methods of use thereof suitable for calibrating dual energy imaging systems.

According to one aspect of the invention, a phantom for use in calibrating a dual energy imaging system is provided that includes a body having at least first and second portions arranged in a through-thickness direction of the body. The first portion defines an anterior surface of the body and comprises a first material simulating soft tissue when imaged with the dual energy imaging system and a second material simulating bone when imaged with the dual energy imaging system. The second portion comprises a third material simulating lung tissue when imaged with the dual energy imaging system and at least a first object embedded in the third material and formed of a fourth material simulating tumor tissue when imaged with the dual energy imaging system. The first and second portions of the body are configured such that the second material in the first portion superimposes the first object in the second portion in the through-thickness direction of the body relative to the anterior surface thereof.

According to another aspect of the invention, a phantom for use in calibrating a dual energy imaging system is provided that includes a body having at least first, second, and third portions arranged in a through-thickness direction of the body. Each of the first and third portions comprises a first material simulating soft tissue when imaged with the dual energy imaging system. The first portion further defines an anterior surface of the body and comprises at least a first elongated object located within the first material thereof and formed of a second material simulating bone when imaged with the dual energy imaging system. The second portion is located between the first and third portions and comprises a third material and at least a first plurality of objects embedded in the third material. The third material simulates lung tissue when imaged with the dual energy imaging system, and the first plurality of objects are formed of a fourth material simulating tumor tissue when imaged with the dual energy imaging system. The first, second, third, and fourth materials each have a homogeneous density and the densities are different from each other, and the first, second, and third portions of the body are configured such that the first elongated object in the first portion superimposes the first plurality of objects in the second portion in the through-thickness direction of the body relative to the anterior surface thereof.

Other aspects of the invention include methods of using a phantom as described above to calibrate a dual energy imaging system for producing bone suppression images.

Technical effects of the phantom and methods described above preferably include the ability to properly calibrate dual energy imaging systems used with radiation therapy in a reproducible and reliable manner.

Other aspects and advantages of this invention will be appreciated from the following detailed description.

BRIEF DESCRIPTION OF THE DRAWINGS

FIG. 1 represents a perspective view of the phantom, FIG. 2 is a representation of the phantom of FIG. 1 with portions of the phantom removed to reveal the relative locations of two rows of simulated tumors and two simulated bones within the phantom when viewed from below the phantom, and FIG. 3 is a cross-sectional view of the phantom taken along section lines 3-3 in FIG. 2 to indicate the vertical locations of the rows of simulated tumors relative to the simulated bones within the phantom.

DETAILED DESCRIPTION OF THE INVENTION

Disclosed herein are phantoms and methods of using the phantoms to calibrate DE subtraction-based imaging systems used to track tumors during radiation therapy of a patient, for example, a linear accelerator (LINAC) with an on-board imager (OBI). To calibrate such equipment, imaging parameters (e.g., kVp, mA) are preferably adjusted to promote clear imaging. To calibrate these parameters associated with DE imaging, the present invention proposes the use of phantoms capable of simulating the chest anatomy of the patient. Such phantoms are preferably capable of simulating various tumor dimensions at different depths, such as located behind the ribs or other bony anatomy. These hidden targets allow for the assessment of bone suppression capabilities of the imaging system and, preferably, targets at various depths may be utilized to evaluate possible scatter contributions.

Figure 1:
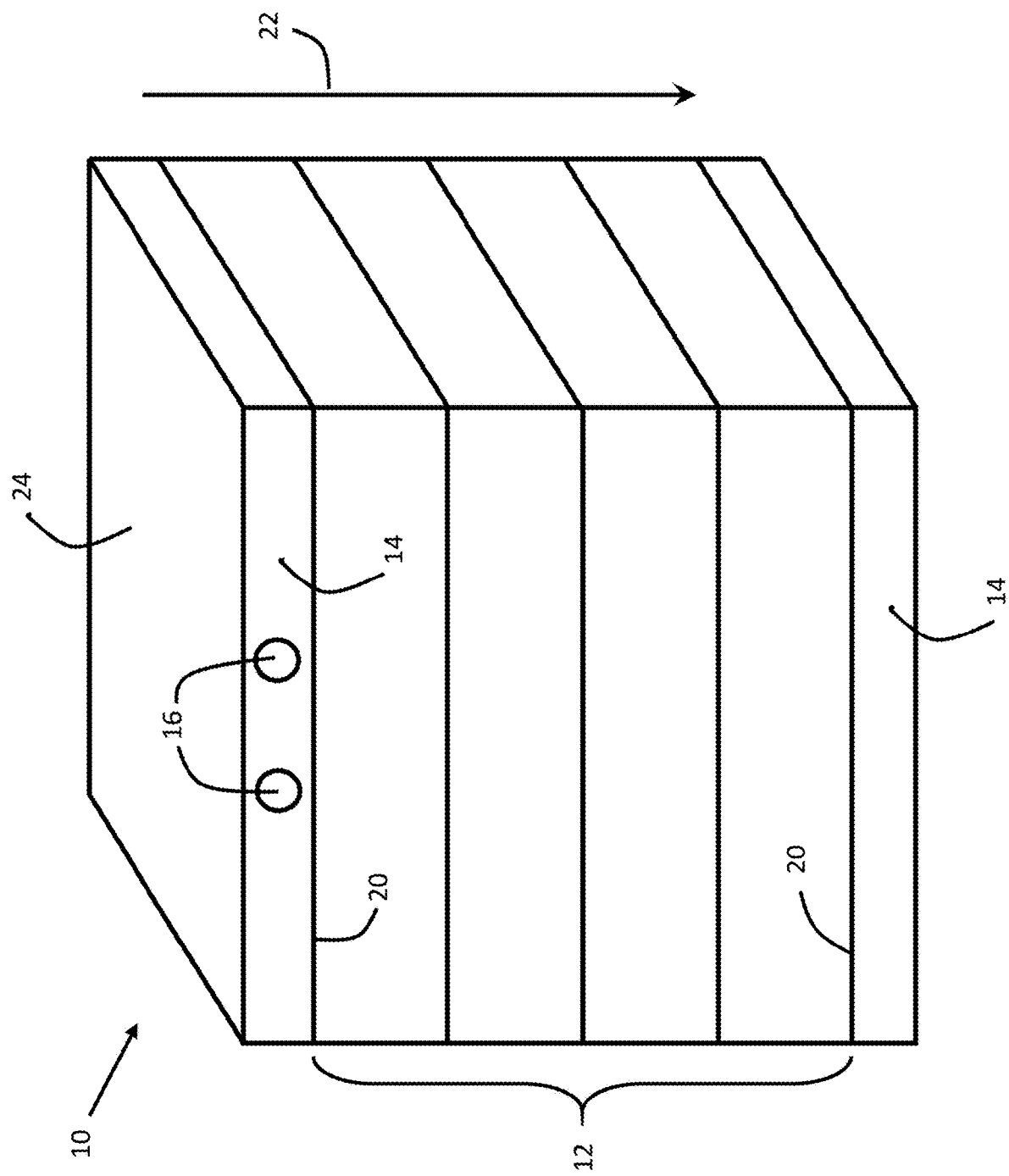
FIGS. 1, 2, and 3 schematically represent a phantom configured for use in calibrating a dual energy imaging system.
Figure 2:
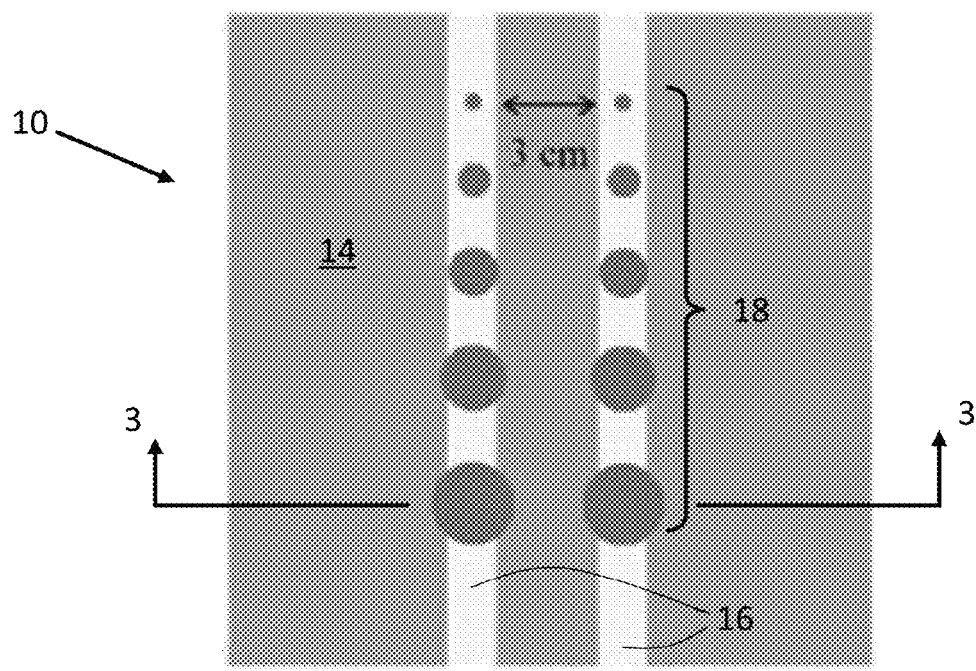
Figure 3:
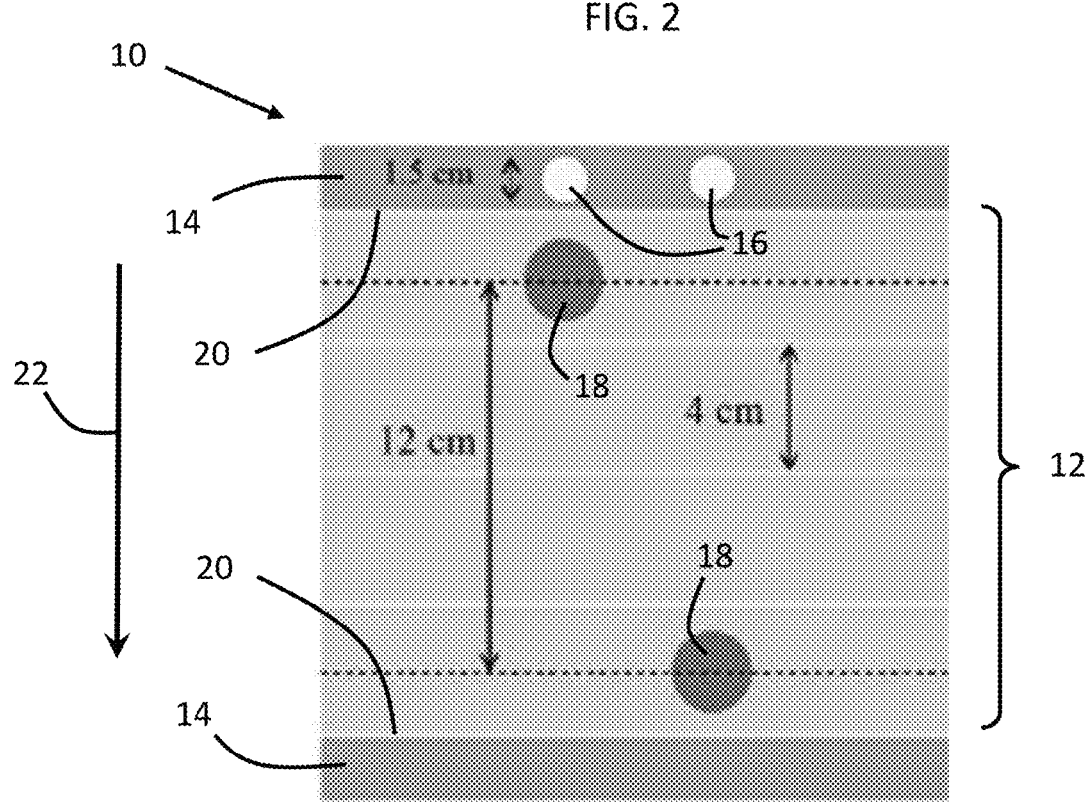

As a nonlimiting example, FIGS. 1, 2, and 3 schematically represent a phantom 10 that was constructed of different synthetic tissue-equivalent materials to define components of the phantom 10 that are capable of simulating bone, lung, soft tissue, and tumors. The components form a body of the phantom 10 and include a lung-equivalent portion 12 sandwiched between two soft tissue-equivalent portions 14, embedded objects in the form of one or more bone-equivalent portions (simulated bones) 16, and embedded objects in the form of one or more simulated tumors 18 (visible only in FIGS. 2 and 3). The lung-equivalent and soft tissue-equivalent portions 12 and 14 are arranged to define two roughly planar interfaces 20 that are generally parallel to the uppermost and lowermost surfaces of the body defined by, respectively, the upper and lower soft tissue-equivalent portions 14 as viewed in FIG. 1. The surface of the body defined by the upper soft tissue-equivalent portion 14 is referred to herein as the anterior surface 24 of the phantom 10 at which photon beams generated by a dual energy system are directed in a through-thickness direction 22 of the phantom 10 to perform a dual imaging technique.

To simulate their respective tissues, the four components of the phantom 10 identified in FIGS. 1-3, namely, the lung-equivalent portion 12, the soft tissue-equivalent portions 14, the bone-equivalent portions 16, and the simulated tumors 18, each have a relatively uniform or homogeneous density ($\rho$) that is different from those of the other components. The bone-equivalent portions 16 are preferably denser than all other components of the phantom 10, i.e., denser than the portions 12 and 14 and the simulated tumors 18, and the lung-equivalent portion 12 is the least dense of the components of the phantom 10. In the particular nonlimiting embodiment of the phantom 10 that was constructed for investigations discussed below, the components of the phantom 10 were, from most dense to least dense, the bone-equivalent portions 16, the simulated tumors 18, the soft tissue-equivalent portions 14, and the lung-equivalent portion 12. In this particular phantom 10, the densities of the components were $\rho=0.31$ g/cm$^3$ for a lung-equivalent material used to form the lung-equivalent portion 12, $\rho=1.03$ g/cm$^3$ for a soft tissue-equivalent material used to form the soft tissue-equivalent portions 14, $\rho=1.6$ g/cm$^3$ for a bone-equivalent material used to form the bone-equivalent portions 16, and $\rho=1.045$ to 1.061 g/cm$^3$ for a tumor-equivalent material used to form the simulated tumors 18.

Although various dimensions are foreseeable and within the scope of the invention, the phantom 10 was constructed to comprise (stacked vertically in FIG. 1) a 16 cm-thick lung-equivalent portion 12 constructed of four layers of the lung-equivalent material. The two soft tissue-equivalent portions 14 were each constructed of a 2 cm-thick layer of the soft tissue-equivalent material, resulting in the body of the phantom 10 having a total thickness of 20 cm in its through-thickness direction 22, i.e., normal to the interfaces 20 between lung-equivalent portion 12 and the soft tissue-equivalent portions 14. Additional or fewer layers of tissue-equivalent materials (as a nonlimiting example, increments of 2 cm) may be employed to construct phantoms to simulate patients of various sizes. FIGS. 1, 2, and 3 further represent each of the bone-equivalent portions 16 as elongated and in the shape of a solid cylinder having a diameter of (as indicated in FIG. 3) 1.5 cm. As represented in FIG. 2, the bone-equivalent portions 16 were roughly parallel to each other and spaced apart from each other about 3 cm in a transverse direction to their longitudinal axes to simulate a pair of ribs located in the upper soft tissue-equivalent portion 14 (as viewed in FIG. 1).

The nonlimiting embodiment of the phantom 10 further depicts the simulated tumors 18 as being arranged in two rows, each row containing five simulated tumors 18 of different clinically relevant sizes. The simulated tumors 18 are not visible in FIG. 1 but schematically represented in FIGS. 2 and 3. The simulated tumors 18 were formed of the tumor-equivalent material to have spherical shapes with diameters ranging from 5 to 25 mm, in increments of 5 mm. As represented by the nonlimiting embodiment shown in FIG. 3, the rows of simulated tumors 18 were embedded in the lung-equivalent portion 12 at different depths (2 cm and 14 cm) from an anterior surface of the lung-equivalent portion 12 at its interface 20 with the upper soft tissue-equivalent portion 14 containing the bone-equivalent portions 16. As represented in FIGS. 2 and 3, the phantom 10 was intentionally constructed so that each row of simulated tumors 18 was overlapped (superimposed) by one of the two bone-equivalent portions 16 in the through-thickness direction 22 of the phantom 10, so that a third image could be created using weighted logarithmic subtraction (WLS) in which bone imaging is suppressed and soft tissue/tumor imaging is enhanced.

Though a particular configuration for the phantom 10 is represented in FIGS. 1, 2, and 3, it should be understood that a phantom may be constructed to have any number of simulated tumors of various sizes, quantity, and depths within the phantom 10. As such, the configuration shown in the drawings can be customized and changed to address specific uses or needs. Likewise, although FIGS. 1, 2, and 3 represent the upper soft tissue-equivalent portion 14 as including two simulated ribs extending therethrough, bone-equivalent portions 16 of other shapes, sizes, and quantities may be used. In addition, the phantom 10 may be constructed to include additional aspects representative of the human anatomy, for example, a bone-equivalent material intended to simulate a spine. The phantom 10 may be constructed so that the lung-equivalent and soft tissue-equivalent portions 12 and 14 are bonded together, though more typically the phantom 10 would be constructed so that at least the bone-containing upper soft tissue-equivalent portion 14 can be removed and/or a differently configured upper soft tissue-equivalent portion 14 used to assess optimum performance.

Dual energy imaging is a powerful method to reveal hidden tumors under bone structures in x-ray radiography. Although, it has been widely used in diagnostic settings, its application has been limited in radiotherapy. DE imaging using the OBI on a linear accelerator can enhance real-time tumor tracking and image-guided radiotherapy applications. Currently, implementation of a fast-kV-switching x-ray source is being considered on linear accelerators. Before this application is clinically available, DE imaging parameters should be properly calibrated. Phantoms of the type described above may be used for such calibration and further to evaluate image post-processing methods such scatter correction and noise reduction. The overall design of the phantom 10 depicted in FIGS. 1-3 allows for fast image acquisition and optimization of imaging parameters. Phantoms of the type described above allow physicists to develop standardized protocols and reproducible results, enabling use of the phantoms as part of a comprehensive quality assurance program. As such, the phantoms can be incorporated as part of a clinical quality assurance program.

Figure 4:
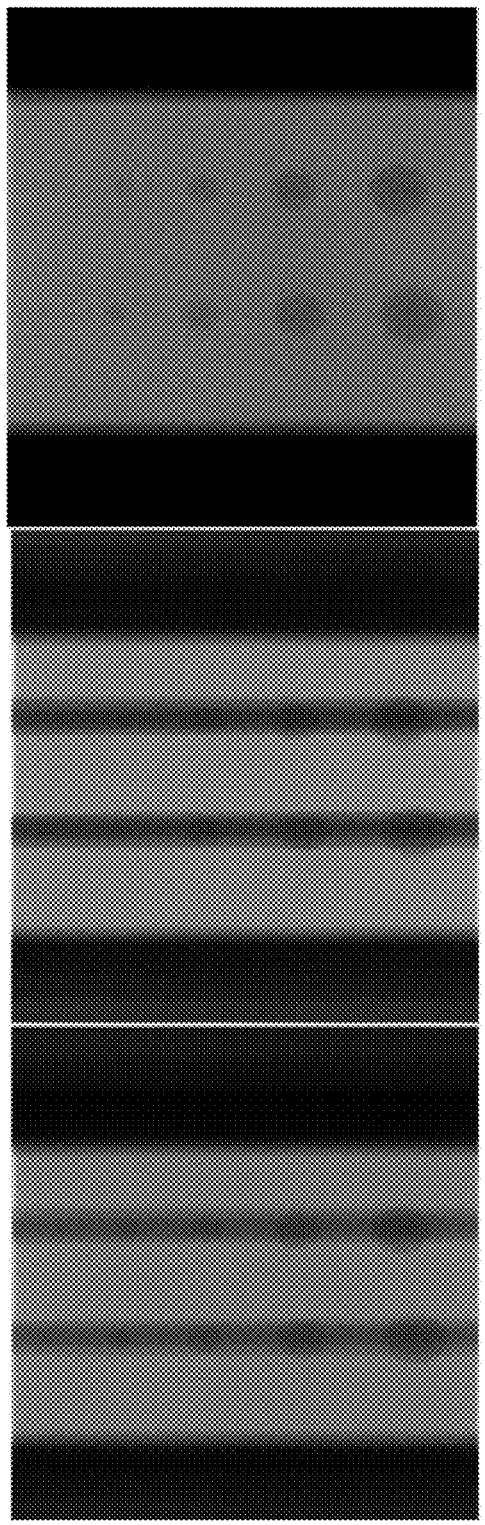
FIG. 4 contains three images of x-rays of a phantom configured as represented in FIGS. 1, 2, and 3, wherein the images include a 120-kVp image (left), a 60-kVp image (middle), and a dual energy image (right).

As a demonstration of such capabilities, FIG. 4 shows three images of x-rays of the phantom 10 represented in FIGS. 1, 2 and 3. The images were generated by orienting the phantom 10 relative to a dual energy imaging system so that photon beams produced by the dual energy system were directed toward the anterior surface 24 of the phantom 10 and in the through-thickness direction 22 of the phantom 10, in other words, toward the soft tissue-equivalent portion 14 containing the bone-equivalent portions 16 and into the lung-equivalent portion 12 therebeneath. FIG. 4 includes a 120-kVp x-ray image (left image), a 60-kVp x-ray image (middle image), and a dual energy image (right image) created from the two x-ray images using WLS to suppress imaging of the bone-equivalent portions 16 and enhance the visualization of the two rows of simulated tumors 18.

The present invention further encompasses methods to automate WLS of dual energy images obtained with phantoms of types as described above using convolutional neural networks (CNN). The automated WLS methods employed an algorithm that decomposes images into basis materials followed by the calculation of weighting factors using the basis materials thicknesses. In one investigation, a CNN architecture was trained to decompose high-low image pairs into basis materials of aluminum (Al) and polymethyl methacrylate (PMMA), which were used to represent bone and soft tissue, respectively. To train the model, a phantom was constructed of Al and PMMA step wedges. Predicted equivalent thicknesses along with projections were used to calculate the effective attenuations of Al at high and low energies. In one approach, the optimal weighting factor was then determined as the ratio of attenuation coefficient for Al at high to low energy. A second approach involved manually determining the weighting factor by iteratively minimizing the contrast between the Al and PMMA materials. A phantom having a construction similar to that described for the phantom of FIGS. 1, 2, and 3 was then constructed of tissue and lung-equivalent epoxy materials, with five simulated spherical tumors (5, 10, 15, 20, and 25 mm) embedded in the lung-equivalent epoxy material. The phantom was imaged using fast-kV dual energy imaging (120 and 60 kVp) on a commercial linear accelerator. The relative contrasts of the tumors were compared between the two approaches for determining the weighting factor for a complete 360° rotation. For all simulated tumors, the analysis demonstrated consistency between the two approaches. The mean relative contrast differences between the two approaches were 3.54%±0.85%, 0.52%±0.22%, 0.05%±0.15%, −0.12%±0.15% and −0.13%±0.14% for 5, 10, 15, 20, and 25 mm targets, respectively. A two sampled t-test demonstrated no-significant differences between the two approaches ($p>0.5$). As such, it was concluded that a technique had been demonstrated to automatically optimize weighting factors for a WLS method, allowing for real-time processing of dual energy images obtained with the phantom.

In another investigation, WLS methods were used to evaluate bone suppression capabilities using dual energy imaging and an on-board imager (OBI) across different commercial linear accelerators. Optimal weighting factors for WLS were utilized to characterize the sensitivity of dual energy imaging across the different machines. A phantom having a construction similar to that described for the phantom of FIGS. 1, 2, and 3 was then constructed with five simulated spherical tumors (5, 10, 15, 20, and 25 mm) embedded in a lung-equivalent material and bone-equivalent portions (simulated ribs) of different diameters (1.5, 3, 5, and 7 cm) embedded in an upper soft tissue-equivalent portion of the phantom. The phantom was imaged at two different energies (120 and 60 kVp) on a linear accelerator manufactured by Varian Edge and three linear accelerators manufactured by True Beam. Bone suppression was performed using WLS by minimizing the contrast between rib and neighboring soft-tissue regions. The optimal weighting factors across linear accelerators were compared and relative tumor contrast was evaluated as a function of weighting factor. The higher weighting factors were observed when the thickness of overlapping bone increased. Weighting factors were 0.533±0.002, 0.541±0.001, 0.547±0.02 and 0.553±0.05 for the bone thicknesses of 1.5, 3, 5 and 7 cm, respectively. The optimal weighting factors across the linear accelerators were 0.546±0.002, 0.535±0.002, 0.549±0.002, and 0.541±0.001 (the last being the Varian Edge linear accelerator). Although weighting factors showed slight variations across linear accelerators, relative tumor contrast was insensitive to these variations which was found to be <1%. As such, it was concluded that weighting factors were consistent across the multiple linear accelerators and produced equivalent tumor contrast using dual energy imaging performed on the phantom.

While the invention has been described in terms of specific or particular embodiments, it should be apparent that alternatives could be adopted by one skilled in the art. For example, a phantom and its components could differ in appearance and construction from the embodiment described herein and shown in the drawings, and appropriate materials could be substituted for those noted. Accordingly, it should be understood that the invention is not necessarily limited to any embodiment described herein or illustrated in the drawings. It should also be understood that the phraseology and terminology employed above are for the purpose of describing the illustrated embodiment, and do not necessarily serve as limitations to the scope of the invention. Therefore, the scope of the invention is to be limited only by the following claims.

The invention claimed is:

1. A phantom for use in calibrating a dual energy imaging system, the phantom comprising:
   a body having at least first and second portions arranged in a through-thickness direction of the body, the first portion defining an anterior surface of the body and comprising a first material simulating soft tissue when imaged with the dual energy imaging system and a second material simulating bone when imaged with the dual energy imaging system, the second portion comprising a third material simulating lung tissue when imaged with the dual energy imaging system and at least a first object embedded in the third material and formed of a fourth material simulating tumor tissue when imaged with the dual energy imaging system;
   wherein the first and second portions of the body are configured such that the second material in the first portion superimposes the first object in the second portion in the through-thickness direction of the body relative to the anterior surface thereof.

2. The phantom of claim 1, wherein the first portion includes at least one object formed of the second material, and the object superimposes the first object in the second portion in the through-thickness direction of the body relative to the anterior surface thereof.

3. The phantom of claim 2, wherein the object formed of the second material is an elongated object.

4. The phantom of claim 2, wherein the first object formed of the fourth material is spherical.

5. The phantom of claim 1, wherein the first object embedded in the third material is one of at least a first plurality of objects formed of the fourth material simulating tumor tissue, and the first plurality of objects differ in size from each other.

6. The phantom of claim 5, wherein the first portion includes at least one elongated object formed of the second material, and the elongated object superimposes each of the first plurality of objects in the through-thickness direction of the body relative to the anterior surface thereof.

7. The phantom of claim 1, wherein the first object embedded in the third material is in one of at least first and second rows of objects that are formed of the fourth material simulating tumor tissue, the first and second rows of objects are embedded in the third material at different depths in the through-thickness direction of the body, the first portion includes at least two elongated objects formed of the second material, and each of the elongated objects superimposes one of the first and second rows of objects in the through-thickness direction of the body relative to the anterior surface thereof.

8. The phantom of claim 1, wherein the first, second, third, and fourth materials each have a homogeneous density and the densities are different from each other.

9. The phantom of claim 1, wherein the second material is denser than the first, third, and fourth materials.

10. The phantom of claim 1, wherein the third material is less dense than the first, second, and fourth materials.

11. The phantom of claim 1, wherein the first, second, third, and fourth materials are, from most dense to least dense, the second material, the fourth material, the first material, and the third material.

12. The phantom of claim 11, wherein the first, second, third, and fourth materials have densities of, respectively, are 1.03 $g/cm^3$, 1.6 $g/cm^3$, 0.31 $g/cm^3$, and 1.045 to 1.061 $g/cm^3$.

13. A method of calibrating a dual energy imaging system with the phantom of claim 1, the method comprising:
    directing photon beams produced by a dual energy system at the anterior surface of the body to produce two radiographic images of the phantom at different energy levels;
    producing a bone suppressed image from the two radiographic images; and
    adjusting operating parameters of the dual energy system based on the bone suppressed image.

14. A method of using the phantom of claim 1, the method comprising:
    directing photon beams produced by a dual energy system at the anterior surface of the body to produce two radiographic images of the phantom at different energy levels;
    producing a plurality of bone suppressed images from the two radiographic images using different weighting factors; and
    determining a preferred weighting factor by comparing relative contrast between regions of the second and third materials in the plurality of bone suppressed images.

15. A phantom for use in calibrating a dual energy imaging system, the phantom comprising:
    a body having at least first, second, and third portions arranged in a through-thickness direction of the body;
    each of the first and third portions comprising a first material simulating soft tissue when imaged with the dual energy imaging system, the first portion further defining an anterior surface of the body and comprising at least a first elongated object located within the first material thereof and formed of a second material simulating bone when imaged with the dual energy imaging system, the second portion being located between the first and third portions and comprising a third material and at least a first plurality of objects embedded in the third material, the third material simulating lung tissue when imaged with the dual energy imaging system, and the first plurality of objects being formed of a fourth material simulating tumor tissue when imaged with the dual energy imaging system, the first, second, third, and fourth materials each having a homogeneous density and the densities are different from each other;
    wherein the first, second, and third portions of the body are configured such that the first elongated object in the first portion superimposes the first plurality of objects in the second portion in the through-thickness direction of the body relative to the anterior surface thereof.

16. The phantom of claim 15, wherein the first plurality of objects differ in size from each other.

17. The phantom of claim 15, wherein the first plurality of objects is a first row of multiple rows of objects, the multiple rows of objects are embedded in the third material at different depths in the through-thickness direction of the body, the first portion includes at least a second elongated object formed of the second material, and each of the first and second elongated objects superimposes one of the multiple rows of objects in the through-thickness direction of the body relative to the anterior surface thereof.

18. The phantom of claim 15, wherein the second material is denser than the first, third, and fourth materials, and the third material is less dense than the first, second, and fourth materials.

19. The phantom of claim 15, wherein the first, second, third, and fourth materials are, from most dense to least dense, the second material, the fourth material, the first material, and the third material.

* * * * *